United States Patent [19]

Nadelson et al.

[11] 3,976,634

[45] Aug. 24, 1976

[54] SUBSTITUTED 7,12-METHANO DIBENZAZOCINES AND 8,13-METHANO DIBENZAZONINES

[75] Inventors: Jeffrey Nadelson, Lake Parsippany; William J. Houlihan, Mountain Lakes, both of N.J.

[73] Assignee: Sandoz, Inc., East Hanover, N.J.

[22] Filed: Mar. 25, 1974

[21] Appl. No.: 454,269

[52] U.S. Cl.................... 260/239 BB; 260/239 D; 260/570.5 R; 260/570.5 C; 424/244
[51] Int. Cl.².............. C07D 223/14; C07D 223/16
[58] Field of Search............... 260/239 BB, 239 D

[56] References Cited
UNITED STATES PATENTS

| | | |
|---|---|---|
| 3,496,165 | 2/1970 | Houlihan et al. ............... 260/239 D |
| 3,498,988 | 3/1970 | Houlihan et al. ............... 260/239 D |
| 3,642,777 | 2/1972 | Houlihan et al. ............... 260/239 D |
| 3,781,270 | 12/1973 | Houlihan et al. ............. 260/239 BB |

OTHER PUBLICATIONS

G. A. Olah "Friedel–Crafts and Related Reactions", vol. II, part 1, p. 519, Interscience, (1964).

*Primary Examiner*—Paul M. Coughlan, Jr.
*Assistant Examiner*—D. B. Springer
*Attorney, Agent, or Firm*—Gerald D. Sharkin; Robert S. Honor; Thomas O. McGovern

[57] ABSTRACT

Substituted 7,12-methano-dibenzazocines and 8,13-methanodibenzazonines, e.g., 7,12-dihydro-6,13-dimethyl-7,12-methano-6H-dibenz [c,f]azocine, are prepared by cyclizing 3-benzylamino or 3-phenethylamino -2-alkyl-indan-1-ols and are useful as anti-inflammatory agents.

11 Claims, No Drawings

SUBSTITUTED 7,12-METHANO DIBENZAZOCINES AND 8,13-METHANO DIBENZAZONINES

This invention relates to 7,12-methano-dibenzazocine and 8,13-methano-dibenzazonine derivatives. In particular, it relates to 13-lower alkyl substituted 7,12-methano-dibenzazocines and 14-lower alkyl substituted 8,13-methano-dibenzazonines, intermediates for their preparation and their use in pharmaceutical compositions.

The compounds of this invention may be represented by the following structural formula:

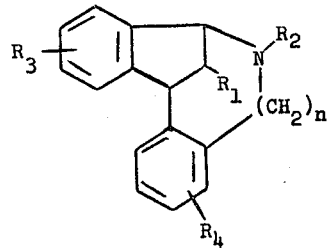

(I)

where
$n$ is 1 or 2
$R_1$ is lower alkyl, i.e., alkyl having 1 to 4 carbon atoms, e.g., methyl, ethyl, isopropyl, butyl and the like;
$R_2$ is hydrogen or lower alkyl as defined above and
$R_3$ and $R_4$ each independently is hydrogen, halo having an atomic weight of about 19 to 35, lower alkyl as defined above, or lower alkoxy, i.e., alkoxy having 1 to 4 carbon atoms, e.g., methoxy, ethoxy, isopropoxy, butoxy and the like,
or a pharmaceutically acceptable acid addition salt thereof.

In the benzazocines and benzazonines of formula (I) having the structures:

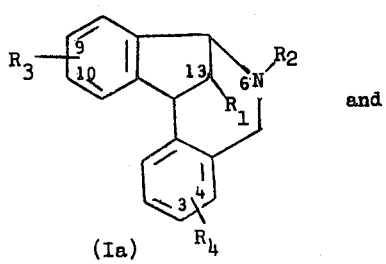

(Ia) and

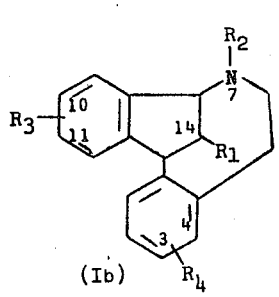

(Ib)

where $R_1$, $R_2$, $R_3$ and $R_4$ are as defined above, $R_3$ and $R_4$ are in the 9, 10 and 3,4 positions respectively of the benzazocines. and in the 10, 11 and 3, 4 positions respectively of the benzazonines. In the preferred compounds, $R_3$ and $R_4$ are both hydrogen, and the compounds in which $R_1$ and $R_2$ are methyl and especially preferred.

The compounds of formula (I) may be prepared in accordance with the folowing reaction scheme:

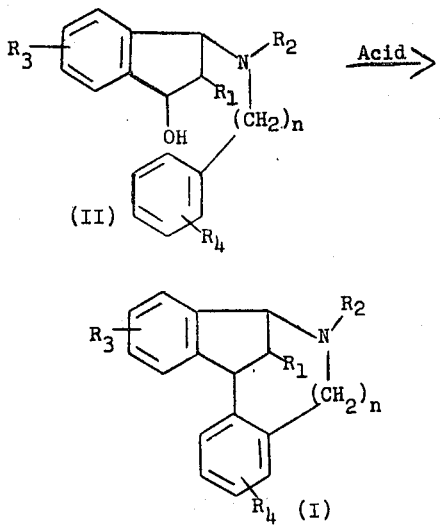

where $n$, $R_1$, $R_2$, $R_3$ and $R_4$ are as defined above.

The compounds of formula (I) are prepared by cyclizing a compound of the formula (II) in a strong acid media. The strongly acid media can be provided by any strong acid but polyphosphoric acid or concentrated sulfuric acid are preferred. Although a solvent is not required, it is preferred that the reaction be carried out in excess acid. The temperature at which the reaction is run is not critical, but it is preferred that the reaction be carried out between about 80°C to 120°C., preferably 100°C with polyphosphoric acid and between about −10°C to +10°C, especially 0°C, with concentrated sulfuric acid. The time of the reaction also is not critical, but it is preferred that the reaction be run for 2 to 8 hours, in particular, about 5 hours. The compounds of formula (I) are isolated by conventional techniques, e.g., extraction and recrystallization.

The compound of formula (II) may be prepared in accordance with the following reaction scheme:

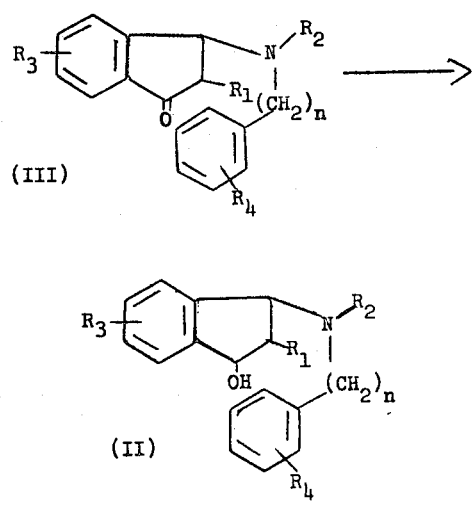

where $n$, $R_1$, $R_2$, $R_3$ and $R_4$ are as defined above.

The compounds of formula (II) are prepared by reducing a compound of the formula (III) with a metal hydride reducing agent in the presence of an inert solvent. The metal hydride reducing agent is preferably lithium aluminum hydride or sodium borohydride. Although the particular inert solvent used is not critical, it is preferred that the reaction be carried out in an ether such as tetrahydrofuran or diethyl ether. When sodium borohydride is used as the reducing agent, a lower alkanol of 1 to 4 carbon atoms, such as methanol, ethanol and the like can be used. The temperature at which the reaction is carried out is not critical, but it is preferred that the reaction be carried out between about −10°C to +10°C., preferably at about 0°C. The time of the reaction also is not critical, but it is preferred that the reaction be run for 2 to 8 hours, in particular about 4 hours. The compounds of formula (II) are isolated by conventional techniques, e.g., evaporation and recrystallization.

The compound of formula (III) may be prepared in accordance with the following reaction scheme:

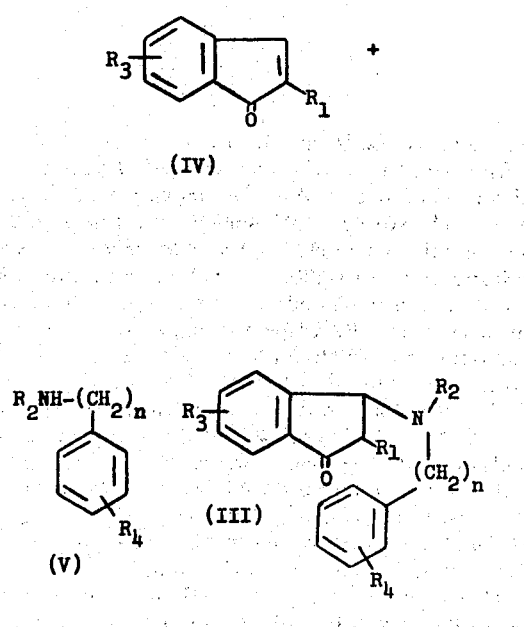

where $n$, $R_1$, $R_2$, $R_3$ and $R_4$ are as defined above.

The compounds of formula (III) are prepared by reacting a compound of the formula (IV) with a compound of the formula (V). Although a solvent is not required, it is preferred that the reaction be carried out in an inert solvent, e.g., a hydrocarbon, such as hexane, heptane, benzene, toluene and the like, or a halogenated hydrocarbon such as chloroform, carbon tetrachloride and the like. The temperature at which the reaction is carried out is not critical, but it is preferred that the reaction be carried out between about 60°C to 180°C, especially at the reflux temperature of the reaction. The time of the reaction also is not critical, but it is preferred that the reaction be run for 10 to 30 hours, especially about 20 hours. It is preferred that the reaction be carried out in an inert atmosphere such as argon, helium, or nitrogen, preferably nitrogen. The compounds of formula (III) are isolated by conventional techniques, e.g., extraction and filtration.

Many of the compounds of formula (IV) and (V) are known and may be prepared by methods disclosed in the literature. The compounds of formula (IV) and (V) not specifically described may be prepared by analogous methods using known starting materials.

The compounds of formula (I) are useful because they possess pharmacological activity in animals. In particular, the compounds of formula (I) are useful as anti-inflammatory agents, as indicated by their activity in rats dosed orally with 25 to 105 milligrams per kilogram of animal body weight of test compound using the acute carrageenan-induced edema procedure substantially as described by Winter (Proc. Soc. Exptl. Biol., 111:544, 1962).

When the compounds are employed for the above utility, they may be combined with one or more pharmaceutically acceptable carriers or adjuvants, and may be administered orally in such forms as tablets, capsules, elixirs, suspensions and the like, or parenterally in the form of an injectable solution or suspension. Depending upon the compound employed and the mode of administration, the exact dosage utilized may vary.

Furthermore, the compounds of formula (I) may be similarly administered in the form of their non-toxic pharmaceutically acceptable acid addition salts. Such salts possess the same order of activity as the free base, are readily prepared by reacting the base with an appropriate acid and accordingly, are included within the scope of the invention. Representative of the acid addition salts are the mineral acid salts, such as the hydrochloride, hydrobromide, sulfate, phosphate and the like and the organic acid salts, such as the succinate, benzoate, acetate, p-toluenesulfonate, benzenesulfonate and the like.

The anti-inflammatory effective dosage of the compounds of formula (I) will depend on the particular compound employed, the method of administration and the severity of the condition being treated. In general, satisfactory results are obtained when these compounds are administered in the treatment of inflammations at a daily dosage of about 2 milligrams to about 200 milligrams per kilogram of animal body weight, preferably orally. This daily dosage is preferably administered 2 to 4 times a day, or in sustained release form. For most large mammals, such as primates, the total daily dosage is from about 150 milligrams to about 1500 milligrams. Dosage forms suitable for internal use comprise from about 37.5 milligrams to about 750 milligrams of the active compound in intimate admixture with a solid or liquid pharmaceutically acceptable carrier or diluent.

A representative formulation suitable for oral administration 2 to 4 times a day in the treatment of inflammation is a capsule prepared by standard encapsulating techniques which contains the following:

| Ingredients | Weight (mg) |
|---|---|
| 7,12-dihydro-6,13-dimethyl-7,12-methano-6H-dibenz[c,f]azocine | 100 |
| Inert solid diluent (starch, lactose, kaolin) | 200 |

EXAMPLE 1

7,12-dihydro-6,13-dimethyl-7,12-methano-6H-dibenz[c,f]azocine

Step A: 3-benzylmethylamino-2-methyl-indan-1-one

A mixture of 10.0 grams (0.069 mole) of 2-methyl-1-indenone and 18.2 grams of N-methylbenzylamine (0.154 mole) in 250 ml of carbon tetrachloride is refluxed under nitrogen for 20 hours. The mixture is cooled and extracted with 2N hydrochloric acid after which the aqueous acid is cooled and made basic by the addition of 50% sodium hydroxide solution. The basic mixture is extracted with ether, dried over magnesium sulfate and evaporated in vacuo. The solid residue is triturated with pentane to give 3-benzylmethylamino-2-methylindan-1-one (m.p. 82°–83°C).

When the above procedure is carried out using an equivalent amount of:

a. benzylamine;
b. N-ethyl-benzylamine;
c. N-methyl-p-chlorobenzylamine;
d. N-methyl-p-methylbenzylamine or
e. N-methyl-p-methoxybenzylamine in place of the N-methylbenzylamine used therein, there is obtained a. 3-benzylamino-2-methylindan-1-one;
b. 3-benzylethylamino-2-methylindan-1-one;
c. 3-(p-chlorobenzylmethylamino)-2-methylindan-1-one;
d. 3-(p-methylbenzylmethylamino)-2-methylindan-1-one or
e. 3-(p-methoxybanzylmethylamino)-2-methylindan--(-p-methoxybenzylmethylamino)--one, respectively.

Following the procedure of this example but using in place of the 2-methyl-1-indanone an equivalent amount of a. 2-isopropyl-1-indenone;
b. 2-methyl-5-chloro-1-indenone;
c. 2-methyl-5-methyl-1-indenone or
d. 2-methyl-5-methoxy-1-indenone, there is obtained a. 3-benzylmethylamino-2-isopropylindan-1-one;
b. 3-benzylmethylamino-2-methyl-5-chloroindan-1-one;
c. 3-benzylmethylamino-2-methyl-5-methylindan-1-one or
d. 3-benzylmethylamino-2-methyl-5-methoxyindan-1-one respectively.

Step B: 3-benzylmethylamino-2-methylindan-1-ol

An ice-cold suspension of 1.5 grams (0.040 mole) of lithium aluminum hydride in 35 ml of dry tetrahydrofuran is treated dropwise over a period of about 30 minutes with a solution of 10.4 grams (0.039 mole) of 3-benzylmethylamino-2-methylindan-1-one in 80 ml of tetrahydrofuran. The mixture is stirred at 0° for 4 hours and then quenched by the addition of ethylacetate, 2N sodium hydroxide and water. The solids are filtered, and the filtrate is dried over magnesium sulfate, filtered and evaporated to yield 3-benzylmethylamino-2-methylindan-1-ol as an oil.

When the above procedure is carried out using an equivalent amount of a. 3-benzylamino-2methylindan-1-one;
b. 3-benzylethylamino-2-methylindan-1-one;
c. 3-(p-chlorobenzylmethylamino)-2-methylindan-1-one;
d. 3-(p-methylbenzylmethylamino)-2-methylindan-1-one;
e. 3-(p-methoxybenzylmethylamino)-2-methylindan-1-one;
f. 3-benzylmethylamino-2-isopropylindan-1-one;
g. 3-benzylmethylamino-2-methyl-5-chloroindan-1-one;
h. 3-benzylmethylamino-2-methyl-5-methylindan-1-one or
i. 3-benzylmethylamino-2-methyl-5-methoxyindan-1-one in place of the 3-benzylmethylamino-2-methylindan-1-one, there is obtained a. 3-benzylamino-2-methylindan-1-ol;
b. 3-benzylethylamino-2-methylindan-1-ol;
c. 3-(p-chlorobenzylmethylamino)-2-methylindan-1-ol;
d. 3-(p-methylbenzylmethylamino)-2-methylindan-1-ol;
e. 3-(p-methoxybenzylmethylamino)-2-methylindan-1-ol;
f. 3-benzylmethylamino-2-isopropylindan-1-ol;
g. 3-benzylmethylamino-2-methyl-5-chloroindan-1-ol;
h. 3-benzylmethylamino-2-methyl-5-methylindan-1-ol or
i. 3-benzylmethylamino-2-methyl-5-methoxyindan-1-ol, respectively.

Step C:
7,12-dihydro-6,13-dimethyl-7,12-methano-6H-dibenzo[c,f]azocine

To 100 grams of polyphosphoric acid at 100°C is added 10 grams (0.0375 mole) of 3-benzylmethylamino-2-methyl-indan-1-ol. The mixture is heated at 100° for 5 hours, and then poured onto ice. The mixture is made basic by the addition of solid sodium hydroxide, and the basic solution is extracted with ether. The ether phase is dried over magnesium sulfate, filtered and treated with gaseous hydrochloric acid. The resulting precipitate is filtered to give 7,12-dihydro-6,13-dimethyl-7,12-methano-6H-dibenz[c,f]azocine hydrochloride (m.p. 258°–259°) after drying.

The 7,12-dihydro-6,13-dimethyl-7,12-methano-6H-dibenz[c,f] azocine of this example is an effective antiinflammatory agent when administered orally to a mammal in need of such treatment at a dose of 100 milligrams 2 to 4 times a day.

Following the above procedure but using an equivalent amount of a. 3-benzylamino-2-methylindan-1-ol;
b. 3-benzylethylamino-2-methylindan-1-ol;
c. 3-(p-chlorobenzylmethylamino)-2-methylindan-1-ol;
d. 3-(p-methylbenzylmethylamino)-2-methylindan-1-ol;
e. 3-(p-methoxybenzylmethylamino)-2-methylindan-1-ol;

f. 3-benzylmethylamino-2-isopropylindan-1-ol;
g. 3-benzylmethylamino-2-methyl-5-chloroindan-1-ol;
h. 3-benzylmethylamino-2-methyl-5-methylindan-1-ol or
i. 3-benzylmethylamino-2-methyl-5-methoxyindan-1-ol, in place of the 3-benzylmethylamino-2-methylindan-1-ol, there is obtained the hydrochloride salt of a. 7,12-dihydro-13-methyl-7,12-methano-6H-dibenz[c,f]azocine (m.p. 301°–303°C);
b. 7,12-dihydro-6-ethyl-13-methyl-7,12-methano-6H-dibenz[c,f]azocine (m.p. 224°–225°C);
c. 2-chloro-7,12-dihydro-6,13-dimethyl-7,12-methano-6H-dibenz[c,f]azocine;
d. 7,12-dihydro-2,6,13-trimethyl-7,12-methano-6H-dibenz[c,f]azocine;
e. 7,12-dihydro-6,13-dimethyl-2-methoxy-7,12-methano-6H-dibenz[c,f]azocine;
f. 7,12-dihydro-13-isopropyl-6-methyl-7,12-methano-6H-dibenz[c,f]azocine (m.p. 268°–269°C);
g. 9-chloro-7,12-dihydro-6,13-dimethyl-7,12-methano-6H-dibenz[c,f] azocine;
h. 7,12-dihydro-6,9,13-trimethyl-7,12-methano-6H-dibenz[c,f]azocine or
i. 7,12-dihydro-6,13-dimethyl-9-methoxy-7,12-methano-6H-dibenz[c,f]azocine, respectively.

EXAMPLE 2

8,13-dihydro-7,14-dimethyl-8,13-methano-7H-dibenz[d,g]azonine

Step A:
3-phenethylmethylamino-2-methyl-indan-1-one

A mixture of 10 grams (0.069 mole) of 2-methyl-1-indenone and 20.8 grams of N-methylphenethylamine (0.154 mole) in 250 ml. of carbon tetrachloride is refluxed under nitrogen for 20 hours. The mixture is cooled and extracted with 2N hydrochloric acid, after which the aqueous acid is cooled and made basic by the addition of 50% sodium hydroxide solution. The basic mixture is extracted with ether, dried over magnesium sulfate and evaporated in vacuo. The solid residue is triturated with pentane to give 3-phenethylmethylamino-2-methyl-indan-1-one.

When the above procedure is carried out using an equivalent amount of:

a. phenethylamine;
b. N-ethyl-phenethylamine;
c. N-methyl-p-chlorophenethylamine;
d. N-methyl-p-methylphenethylamine or
e. N-methyl-p-methoxyphenethylamine in place of the N-methylphenethylamine used therein, there is obtained, a. 3-phenethylamino-2-methylindan-1-one;
b. 3-ethylphenethylamino-2-methylindan-1-one;
c. 3-(p-chlorophenethylmethylamino)-2-methylindan-1-one;
d. 3-(p-methylphenethylmethylamino)-2-methylindan-1-one or
e. 3-(p-methoxyphenethylmethylamino)-2-methylindan-1-one; respectively.

Following the procedure of this example, but using in place of the 2-methyl-1-indenone an equivalent amount of a. 2-isopropyl-1-indenone;
b. 2-methyl-5-chloro-1-indenone;
c. 2-methyl-5-methyl-1-indenone, or
d. 2-methyl-5-methoxy-1-indenone,
there is obtained
a. 3-phenethylmethylamino-2-isopropylindan-1-one;
b. 3-phenethylmethylamino-2-methyl-5-chlorindan-1-one;
c. 3-phenethylmethylamino-2-methyl-5-methylindan-1-one or
d. 3-phenethylmethylamino-2-methyl-5-methoxyindan-1-one, respectively.

Step B: 3-phenethylmethylamino-2-methylindan-1-ol

An ice-cold suspension of 1.5 grams (0.040 mole) of lithium aluminum hydride in 35 ml. of dry tetrahydrofuran is treated dropwise over a period of about 30 minutes with a solution of 10.9 grams (0.039 mole) of 3-phenethylmethylamino-2-methylindan-1-one in 80 ml of tetrahydrofuran. The mixture is stirred at 0° for 4 hours and then quenched by the addition of ethylacetate, 2N sodium hydroxide and water. The solids are filtered, an the filtrate is dried over magnesium sulfate, filtered and evaporated to yield 3-phenethylmethylamino-2-methylindan-1-ol as an oil.

When the above procedure is carried out using an equivalent amount of a. 3-phenethylamino-2-methylindan-1-one;
b. 3-ethylphenethylamino-2-methylindan-1-one;
c. 3-(p-chlorophenethylmethylamino)-2-methylindan-1-one;
d. 3-(p-methylphenethylmethylamino)-2-methylindan-1-one;
e. 3-(p-methoxyphenethylmethylamino)-2-methylindan-1-one;
f. 3-phenethylmethylamino-2-isopropylindan-1-one;
g. 3-phenethylmethylamino12-methyl--phenethylmethylamino--chlorindan-1-one;
h. 3-phenethylmethylamino-2-methyl-5-methylindan-1-one or
i. 3-phenethylmethylamino-2-methyl-5-methoxyindan-1-one in place of the 3-phenethylmethylamino-2-methylindan-1-one, there is obtained
a. 3-phenethylamino-2-methylindan-1-ol;
b. 3-ethylphenethylamino-2-methylindan-1-ol;
c. 3-(p-chlorophenethylmethylamino)-2-methylindan-1-ol;
d. 3-(p-methylphenethylmethylamino)-2-methylindan-1-ol;
e. 3-(p-methoxyphenethylmethylamino)-2-methylindan-1-ol,
f. 3-phenethylmethylamino-2-isopropylindan-1-ol;
g. 3-phenethylmethylamino-2-methyl-5-chloroindan-1-ol;
h. 3-phenethylmethylamino-2-methyl-5-methylindan-1-ol or
i. 3-phenethylmethylamino-2-methyl-5-methoxyindan-1-ol, respectively.

Step C:
8,13-dihydro-7,14-dimethyl-8,13-methano-7H-dibenzo[d,g]azonine

To 100 grams of polyphosphoric acid heated at 100°C is added 10.5 grams (0.0375 mole) of 3-phenethylmethylamino-2-methylindan-1-ol. The mixture is heated at 100° for 5 hours, and then poured onto ice. The mixture is made basic by the addition of solid sodium hydroxide, and the basic solution is extracted with ether. The ether phase is dried over magnesium sulfate, filtered and evaporated. The residue is then triturated with pentane to give 8,13-dihydro-7,14-dimethyl-8,13-methano-7H-dibenz[d,g]azonine (m.p. of base 84°–85.5°C).

When the above reaction is carried out using an equivalent amount of a. 3-phenethylamino-2-methylindan-1-ol;
b. 3-ethylphenethylamino-2-methylindan-1-ol;
b. 3-(p-chlorophenethylmethylamino)-2-methylindan-1-ol;
d. 3-(p-methylphenethylmethylamino)-2-methylindan-1-ol;
e. 3-(p-methoxyphenethylmethylamino)-2-methylindan-1-ol;
f. 3-phenethylmethylamino-2-isopropylindan-1-ol;
g. 3-phenethylmethylamino-2-methyl-5-chloroindan-1ol;
h. 3-phenethylmethylamino-2-methyl-5-methylindan-1-ol or
i. 3-phenethylmethylamino-2-methyl-5-methoxyindan-1-one, in place of the 3-phenethylmethylamino-2-methylindan-1-ol, there is obtained:
a. 8,13-dihydro-14-methyl-8,13-methanol-7H-dibenz[d,g]azonine;
b. 8,13-dihydro-7-ethyl-14-methyl-8,13-methano-7H-dibenz[d,g]azonine;
c. 2-chloro-8,13-dihydro-7,14-dimethyl-8,13-methano-7H-dibenz[d,g]azonine;
d. 8,13-dihydro-2,7,14-trimethyl-8,13-methano-7H-dibenz[d,g]azonine;
e. 8,13-dihydro-7,14-dimethyl-2-methoxy-8,13-methano-7H-dibenz[d,g]azonine;
f. 8,13-dihydro-14-isopropyl-7-methyl-8,13-methano-7H-dibenz[d,g]azonine (m.p. of hydrochloride salt, 252°–253°C);
g. 10-chloro-8,13-dihydro-7,14-dimethyl-8,13-methano-7H-dibenz[d,g]azonine;
h. 8,13-dihydro-7,10,14-trimethyl-8,13-methano-7H-dibenz[d,g]azonine or
i. 8,13-dihydro-7,14-dimethyl-10-methoxy-8,13-methano-7-dibenz[d,g]azonine; respectively.

What is claimed is:
1. A compound of the formula:

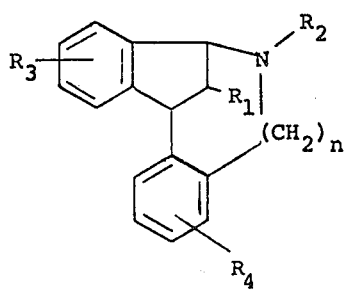

where
$n$ is 1 or 2;
$R_1$ is having alkyl havin 1 to 4 carbon atom
$R_2$ is hydrogen or lower alkyl having 1 to 4 carbon atoms and
$R_3$ and $R_4$ each independently is hydrogen, halo having an atomic weight of about 19 to 35, lower alkyl having 1 to 4 carbon atoms or lower alkoxy having 1 to 4 carbon atoms or
a pharmaceutically acceptable acid addition salt thereof.

2. A compound according to claim 1 in the form of a pharmaceutically acceptable acid addition salt.

3. A compound according to claim 1, having the formula

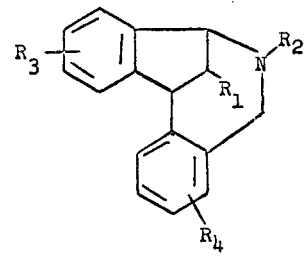

where $R_1$, $R_2$, $R_3$ and $R_4$ are as defined in claim 1.

4. A compound according to claim 1, having a formula

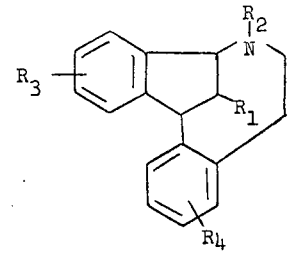

where $R_1$, $R_2$, $R_3$, and $R_4$ are as defined above.

5. A compound according to claim 1 in which $R_3$ and $R_4$ are hydrogen.

6. A compound according to claim 1, in which $R_1$ and $R_2$ are methyl.

7. The compound according to claim 1 which is 7,12-dihydro-6,13-dimethyl-7,12-methano-6H-dibenz[c,f]azocine.

8. The compound according to claim 1 which is 7,12-dihydro-13-methyl-7,12-methano-6H-dibenz[c,f]azocine.

9. The compound according to claim 1 which is 7,12-dihydro-13-isopropyl-6-methyl-7,12-methano-6H-dibenz[c,f]azocine.

10. The compound according to claim 1 in which is 8,13-dihydro-7,14-dimethyl-8,13-methano-7H-dibenz[d,g]azonine.

11. The compound according to claim 1 which is 8,13-dihydro-14-isopropyl-7-methyl-8,13-methano-7H-dibenz[d,g]azonine.

* * * * *